US012751666B2

(12) United States Patent
Safar

(10) Patent No.: US 12,751,666 B2
(45) Date of Patent: Oct. 6, 2026

(54) POSTURE TRAINING

(71) Applicant: Samir Hanna Safar, Solana Beach, CA (US)

(72) Inventor: Samir Hanna Safar, Solana Beach, CA (US)

(73) Assignee: Lori Ann Safar, Oceanside, CA (US)

( * ) Notice: Subject to any disclaimer, the term of this patent is extended or adjusted under 35 U.S.C. 154(b) by 388 days.

(21) Appl. No.: 18/233,062

(22) Filed: Aug. 11, 2023

(65) Prior Publication Data

US 2025/0049392 A1 Feb. 13, 2025

(51) Int. Cl.

| | |
|---|---|
| ***A61B 5/00*** | (2006.01) |
| ***A61B 5/11*** | (2006.01) |
| *A61B 90/00* | (2016.01) |

(52) U.S. Cl.

CPC ............ *A61B 5/486* (2013.01); *A61B 5/1116* (2013.01); *A61B 5/6832* (2013.01); *A61B 5/7455* (2013.01); *A61B 2090/064* (2016.02); *A61B 2505/09* (2013.01)

(58) Field of Classification Search

CPC ..... A61B 5/486; A61B 5/1116; A61B 5/6832; A61B 5/7455; A61B 2090/064; A61B 2505/09; A61B 5/6823; A61B 5/4561

See application file for complete search history.

(56) References Cited

U.S. PATENT DOCUMENTS

| | | | | |
|---|---|---|---|---|
| 5,018,511 A * | 5/1991 | Yokoi | ................ | A61H 23/0254 601/111 |
| 2003/0009116 A1* | 1/2003 | Luettgen | ................ | A61H 19/34 601/72 |
| 2013/0143723 A1* | 6/2013 | Bender | .................. | A63B 21/02 482/121 |
| 2015/0217162 A1* | 8/2015 | Richardson | ............ | A63B 71/06 482/8 |
| 2016/0198995 A1* | 7/2016 | Yeung | ................... | A61B 5/1118 600/595 |
| 2016/0310065 A1* | 10/2016 | Arif | ...................... | A61B 5/1116 |
| 2017/0036066 A1* | 2/2017 | Chahine | ................. | A41D 1/002 |
| 2018/0184735 A1* | 7/2018 | Longinotti-Buitoni | ...................... | A61B 5/282 |
| 2018/0228403 A1* | 8/2018 | Li | ........................ | A61B 5/7405 |
| 2019/0008447 A1* | 1/2019 | Lacker | ................. | A61B 5/0002 |
| 2019/0160652 A1* | 5/2019 | Mahoney | .................. | A61F 2/68 |
| 2020/0000377 A1* | 1/2020 | Ly | ........................ | A61B 5/0022 |
| 2020/0093679 A1* | 3/2020 | Sonar | ....................... | G01L 5/228 |
| 2020/0113725 A1* | 4/2020 | Petterson | ................ | A61F 5/024 |

* cited by examiner

*Primary Examiner* — Jack Yip
(74) *Attorney, Agent, or Firm* — Samir Hanna Safar

(57) ABSTRACT

A posture training device comprises a skin-force sensor configured to detect a deviation of a user's posture from a reference posture, and a tactile feedback arm coupled to the skin-force sensor. The tactile feedback arm is configured to cooperate with the skin-force sensor to deliver tactile feedback to the user in response to the skin-force sensor detecting the deviation of the user's posture from the reference posture.

9 Claims, 13 Drawing Sheets

FIG. 13A
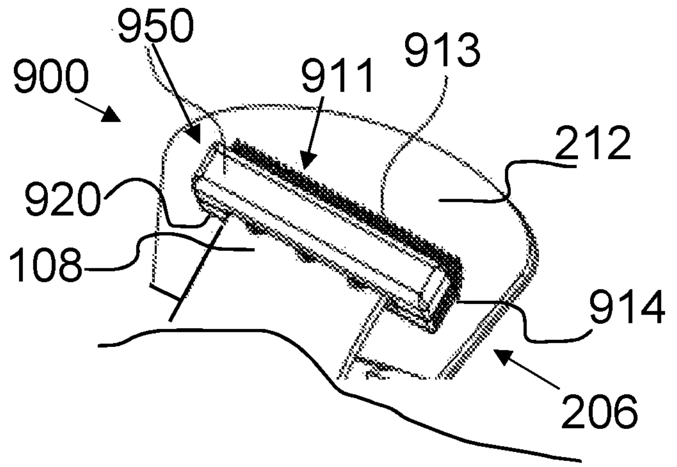
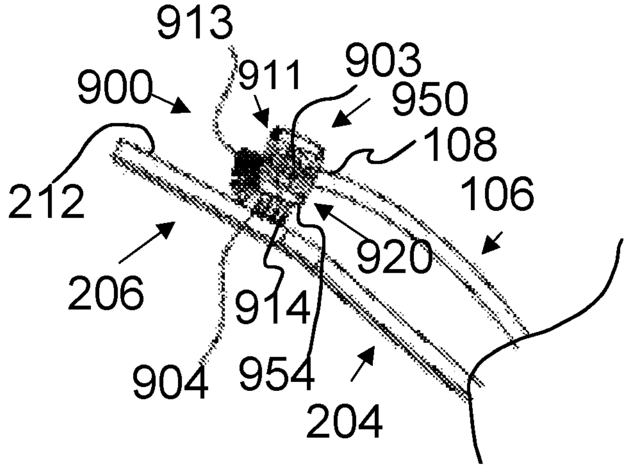
FIG. 13B
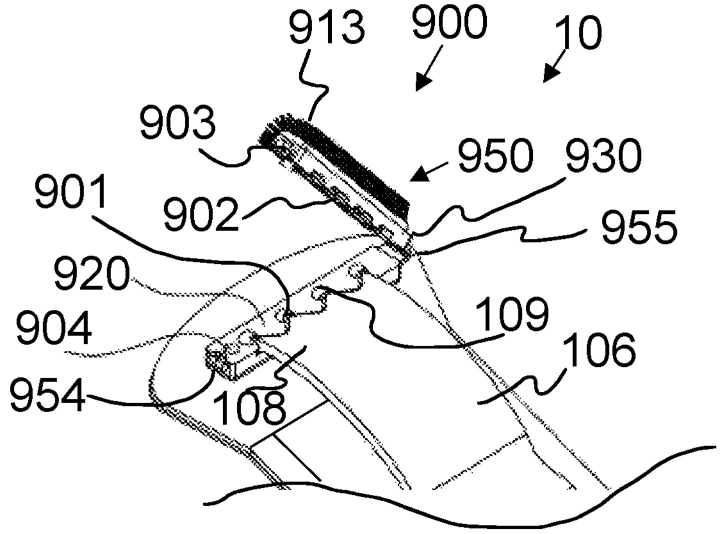
FIG. 13C

POSTURE TRAINING

FIELD OF THE INVENTION

The disclosure relates to posture training. In particular, the present disclosure relates to wearable posture training devices that sense changes in a wearer's posture and deliver tactile feedback in response to the sensed changes.

BACKGROUND OF THE INVENTION

Poor posture and associated health problems are becoming increasingly prevalent due to today's sedentary lifestyles. Office workers spend long hours sitting at desks. Students spend hours hunched over laptops and textbooks. Those with medical conditions such as scoliosis or osteoporosis may inherently have difficulty maintaining good posture. Many people are not aware of their poor posture habits until they begin experiencing symptoms due to prolonged periods of strain on their muscles, ligaments, and joints. Symptoms may include back, neck and shoulder pain, headache, arthritis, digestive problems, and a host of other health issues.

Traditional approaches to correcting and/or preventing poor posture include the use of wearable items such as braces, belts, and trusses to mechanically enforce a desired posture. While such devices are useful, they have some drawbacks in that they can be uncomfortable, cumbersome, or aesthetically objectionable. They may restrict range of motion, interfering with routine daily activities such as sitting at a desk or driving a car. Further, habitual use of immobilization devices may lead to imbalances and muscle weakness due to over-reliance on the devices and under-reliance on the muscles themselves.

SUMMARY OF THE INVENTION

A posture training device comprises a skin-force sensor configured to detect a deviation of a user's posture from a reference posture, and a tactile feedback arm coupled to the skin-force sensor. The tactile feedback arm is configured to cooperate with the skin-force sensor to deliver tactile feedback to the user in response to the skin-force sensor detecting the deviation of the user's posture from the reference posture.

The disclosed embodiments provide novel compact, discreet wearable devices for posture training. The disclosed devices gently and unobtrusively alert a wearer when the wearer's posture deviates from a reference posture by delivering tactile feedback. This encourages the wearer to actively engage their muscles to correct the deviation and return to the reference posture. Posture training devices within the scope of the disclosure are compact, unobtrusive and can be worn under most types of clothing without causing visible bulges or lines.

Advantageously, disclosed embodiments are free of straps, belts, trusses and the like. Accordingly, the disclosed posture training devices do not immobilize, restrict, or interfere with the user's movements allowing the user to comfortably perform routine daily tasks while wearing them. Further, some embodiments are entirely mechanical in their operation and free of electronic components, wires, or batteries. This makes them simple to attach, lightweight and environmentally friendly.

BRIEF DESCRIPTION OF THE DRAWINGS

For a complete understanding reference should be made to the following detailed description and the accompanying drawings wherein:

FIG. 13A is a perspective view of an alternative implementation of the tactile feedback arm of the posture training device;

FIG. 13B a side elevation view of the alternative implementation of the tactile feedback arm of the posture training device illustrated in FIG. 13A; and FIG. 13C is a perspective view of the alternative implementation of the tactile feedback arm of the posture training device illustrated in FIGS. 13A and 13B.

DETAILED DESCRIPTION

Exemplary embodiments of the invention will now be described in detail with reference to the accompanying drawings.

Figure 1A:
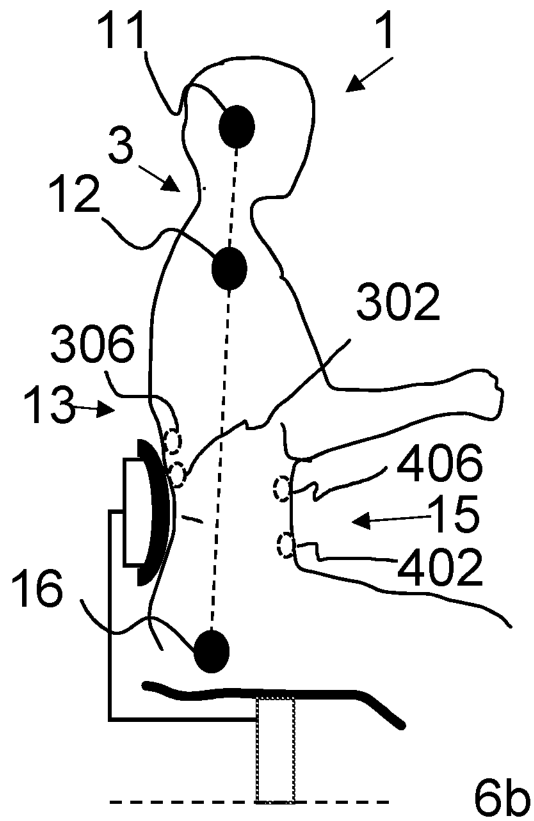
FIG. 1A is a pictorial diagram illustrating a user in a sitting reference posture.

As used herein the terms 'reference posture' a refers to an upright posture, which may be sitting or standing. For example, a reference posture may be an upright sitting posture as illustrated in FIG. 1A. In the reference posture, the user's head 11 is generally aligned with the user's shoulders 12 and the user's hips 16 such that natural curves of the user's spine at the neck 3 and back 13 are maintained. In the reference posture the user's abdominal region 15 is generally flat and straight.

In the reference posture the user's musculoskeletal system maintains the user's skin in a reference skin state. For example, skin portion 306 and 302 on the user's back are in a relative position largely determined by the alignment of the spine in which the head 11, shoulder's 12 and hips 16 are generally in line. Likewise, skin portions 402 and 406 in the user's abdominal area are determined by the alignment of head 11, shoulder's 12 and hips 16.

Figure 1B:
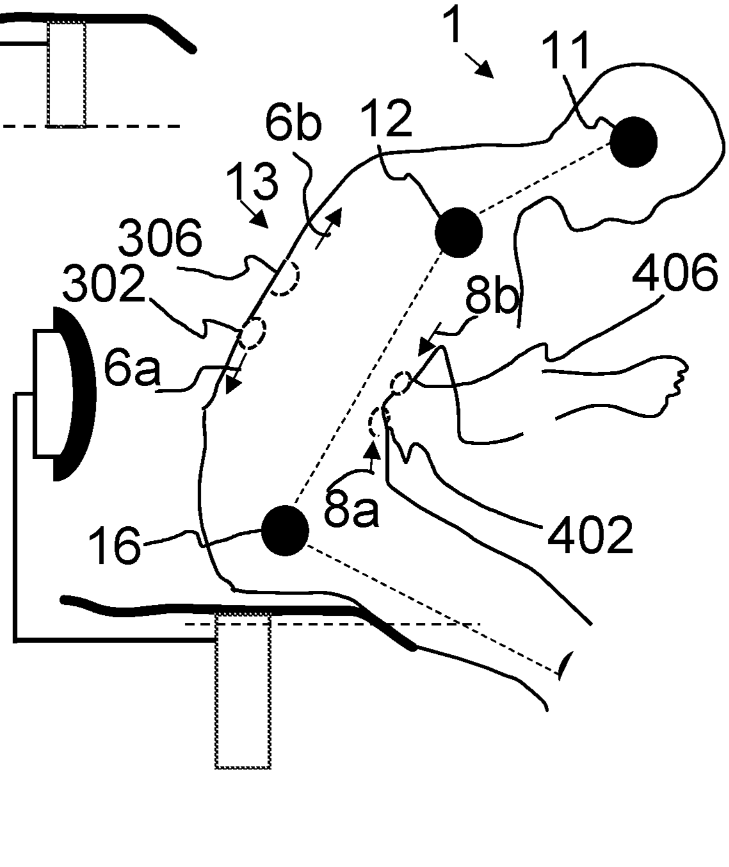
FIG. 1B is a pictorial diagram illustrating a posture that deviates from the reference posture shown in FIG. 1A.

FIG. 1B is a pictorial diagram illustrating user 1 in a posture that deviates from the reference posture shown in FIG. 1A. In the 'slouching' posture shown in FIG. 1A the user's head is forward of the user's shoulders 12. Shoulder's 12 are forward of the hips 16.

In this position the user's musculoskelatal system exerts an expansion force 6*b* on skin portion 306, and 6*a* on skin portion 302 of the user's back. In this posture the user's back 13 is lengthened, expanding the skin. The expansion forces 6a, 6b tend to move skin portion 306 and skin portion 302 away from one another. At the same time, the user's abdominal region 15 is shortened, contracting the skin in abdominal region 15. In other words, in the slouching posture shown in FIG. 1B, contraction forces 8a, 8b in the abdominal region 15 tend to move skin portion 402 and 406 closer together.

Figure 2A:
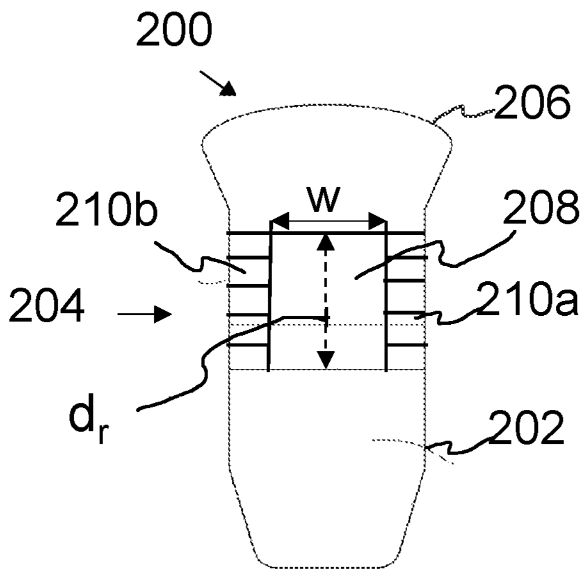
FIGS. 2A-2C are top views of a skin-force sensor according to the disclosure.
Figure 2B:
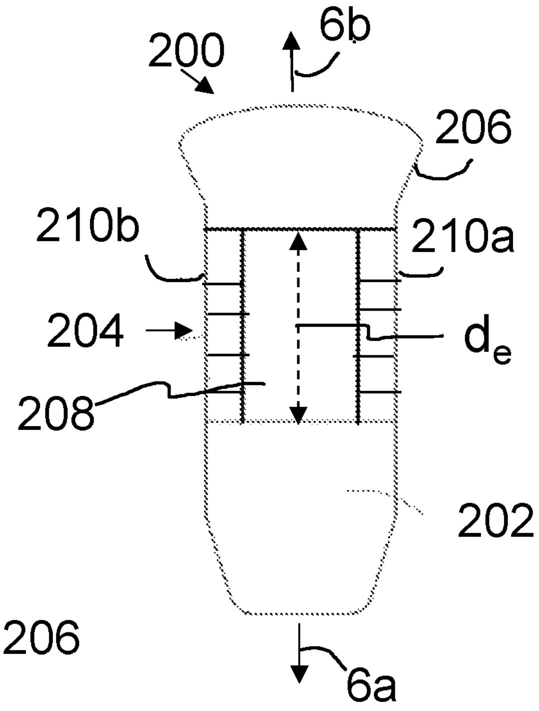
Figure 2C:
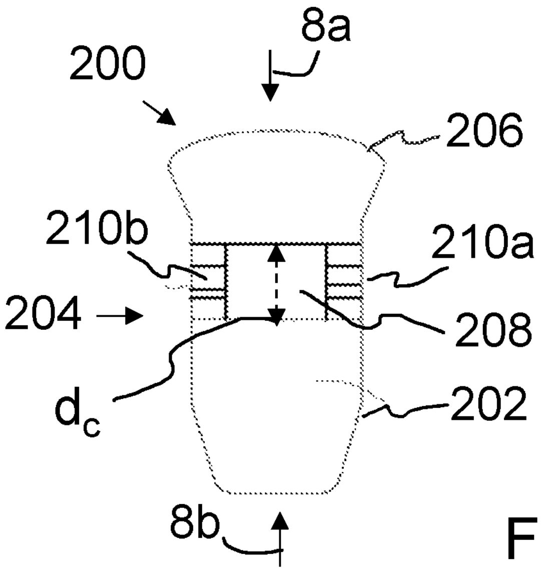

An example posture training device comprises a skin-force sensor and a tactile feedback arm in a cooperative arrangement. In order to facilitate description of the operation of the posture training device, the operation of the skin force sensor alone will first be described. FIGS. 2A-2C are top plan views of an example skin-force sensor 200 of a posture training device 10 according to the disclosure. Skin-force sensor 200 comprises a proximal sensor portion 202, a distal sensor portion 206 and an elastic intermediate portion 204.

Elastic intermediate portion 204 comprises a first elastic part 210a extending along a first side of skin-force sensor 200, and a second elastic parts 210b extending along a side of skin-force sensor 200 opposite the first side. In this specification, the terms 'elastic' refers to an ability of an object or material to resist a distorting force and to return to its resting (original) size and shape when that influence or force removed.

FIG. 2A shows skin-force sensor 200 in a resting (original) state. In the resting state proximal sensor portion 202 and distal sensor portion 206 are separated by a resting distance dr which corresponds to the resting lengths of first and second elastic parts 210a and 210b.

FIG. 2B shows the sensor of FIG. 2A in an expanded state, i.e., lengthened from the resting length shown in FIG. 2A due to a tension or pulling force, 6a, 6b. A tension force is a force that is working to lengthen a piece. In the expanded state proximal sensor portion 202 is separated from distal sensor portion 206 by an expanded distance de, which corresponds to the lengths of first and second elastic parts 210a and 210b in their expanded state. Elastic intermediate portion 204 permits deviation from the resting separation in response to the deviation of the user from the reference posture.

FIG. 2C shows skin-force sensor 200 in a compressed or contracted state, i.e., having a length shortened from its length in the resting state (shown in FIG. 2A) due to application of a compression force 8a, 8b. A compression force is a force that is working to shorten a piece. In the compressed or contracted state proximal sensor portion 202 is separated from distal sensor portion 206 by a contracted distance dc, which corresponds to the lengths of first and second elastic parts 210a and 210b in their contracted state. Elastic intermediate portion 204 permits proximal sensor portion 202 and distal sensor portion 206 to deviate from their resting separation dr in response to deviation of the user from the reference posture.

In some implementations, proximal sensor portion 202 and distal sensor portion 206 are formed of a rubber material. However, the disclosure is not limited to implementations using rubber materials. Other materials are suitable. For example, alternative suitable materials include plastic, which may be a soft plastic that is sufficiently pliable to conform generally to the contours of the body. While rigid plastic could be used, soft plastic is more in general more comfortable to wear next to the skin.

In some implementations, elastic intermediate portion 204 may be constructed of a non-elastic foldable or collapsible material. In some implementations first and second elastic parts 210a, 210b are formed of a corrugated material such as corrugated cardboard. In these implementations, elastic parts 210a, 210b are expandable by unfolding from their original position in response to pulling forces 6a, 6b and contractible by folding from their resting position in response to compression forces 8a, 8b. In alternative embodiments first and second elastic parts 210a and 210b may comprise elastic strips, or any other suitable material with elastic properties.

Figure 3A:
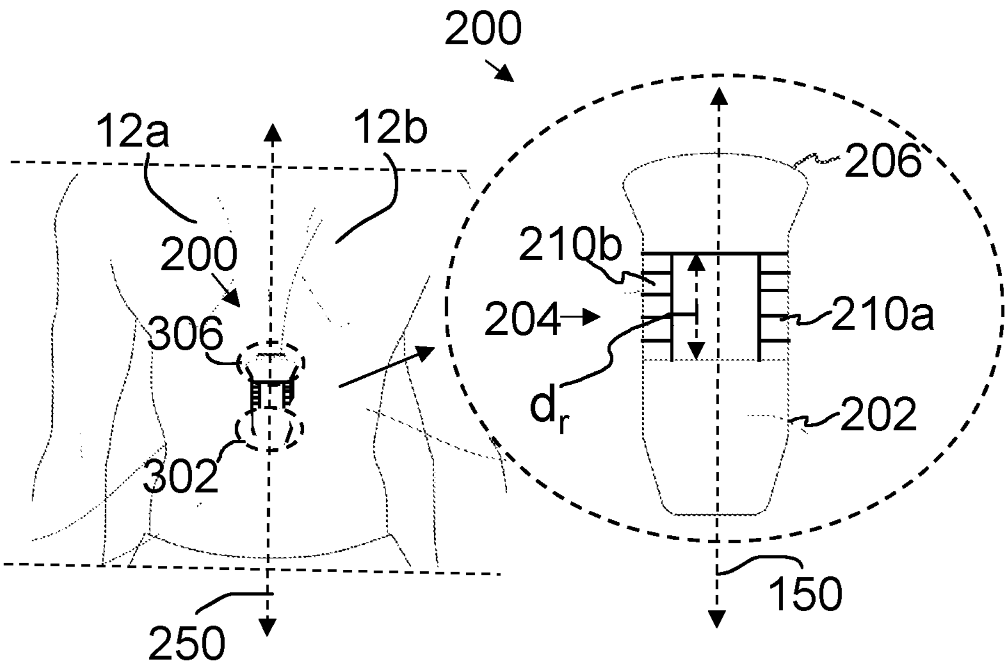
FIGS. 3A-3B are pictorial diagrams showing the skin-force sensor of FIGS. 2A-2C disposed on a user's back.
Figure 3B:
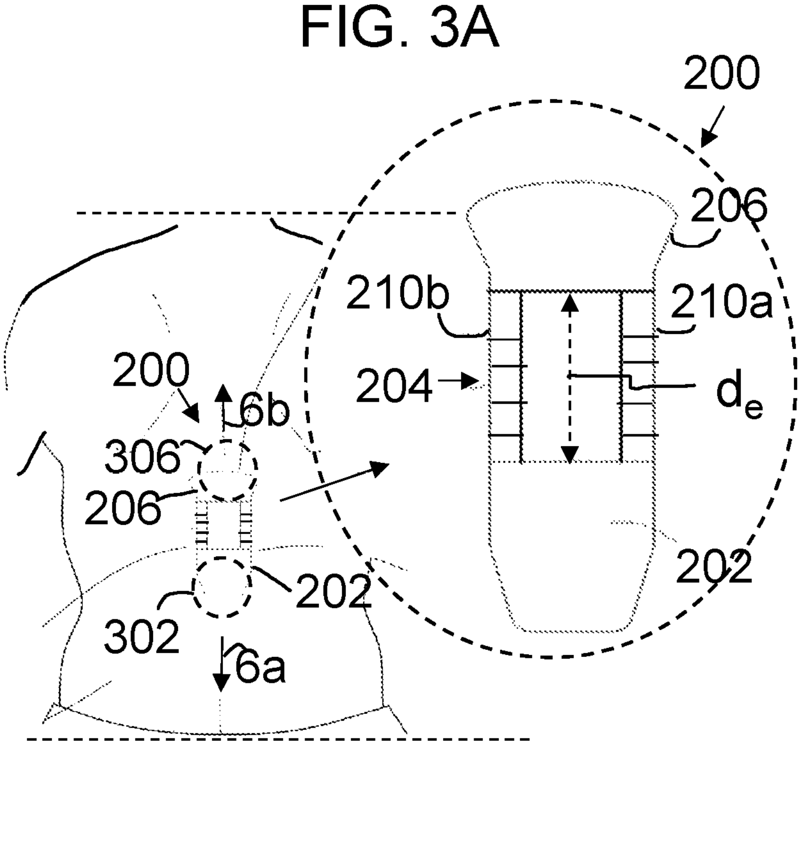

FIGS. 3A and 3B are pictorial diagrams skin-force sensor 200 disposed on a user's back to detect a deviation of the user's posture from a reference posture. Skin-force sensor alone only detects the deviation of the user's posture. It does not by itself provide tactile feedback.

FIG. 3A shows skin-force sensor 200 applied to the user's back with the user in the reference posture depicted in FIG. 1A and skin-force sensor 200 in the resting state shown in FIG. 2A. Skin-force sensor 200 is oriented with a central longitudinal axis 150 of the device generally aligned with a central longitudinal axis 250 of the user's body between the user's scapula 12a, 12b.

Proximal sensor portion 202 is adhered to a corresponding portion of the skin on the user's back, e.g., skin portion 302. Distal sensor portion 206 is likewise adhered to a corresponding portion of the user's skin, e.g., skin portion 306. In the resting state, proximal sensor portion 202 is spaced from distal sensor portion 206 by a distance dr. Distance dr corresponds to the length of elastic intermediate parts 210a, 210b in their resting states.

FIG. 3B illustrates the user in a slouching posture as illustrated in FIG. 1B. This posture deviates from the reference posture depicted in FIG. 1A. When the user slouches the natural curvature of the user's spine increases from its curvature in the upright sitting position. The back muscles exert a pulling force 6b in an upward direction on skin portion 306, and a pulling force 6a in a downward on skin portion 302. Pulling forces 6a, 6b on skin portions 302, 306 pull proximal sensor portion 202 away from distal sensor portion 206. Elastic intermediate portion 204 expands in response to the relative motion of proximal sensor portion 202 and distal sensor portion 206, thereby increasing the separation distance to de. In that manner, skin-force sensor 200 detects deviation of the user's posture from the reference posture when applied to the user's back.

Figure 4A:
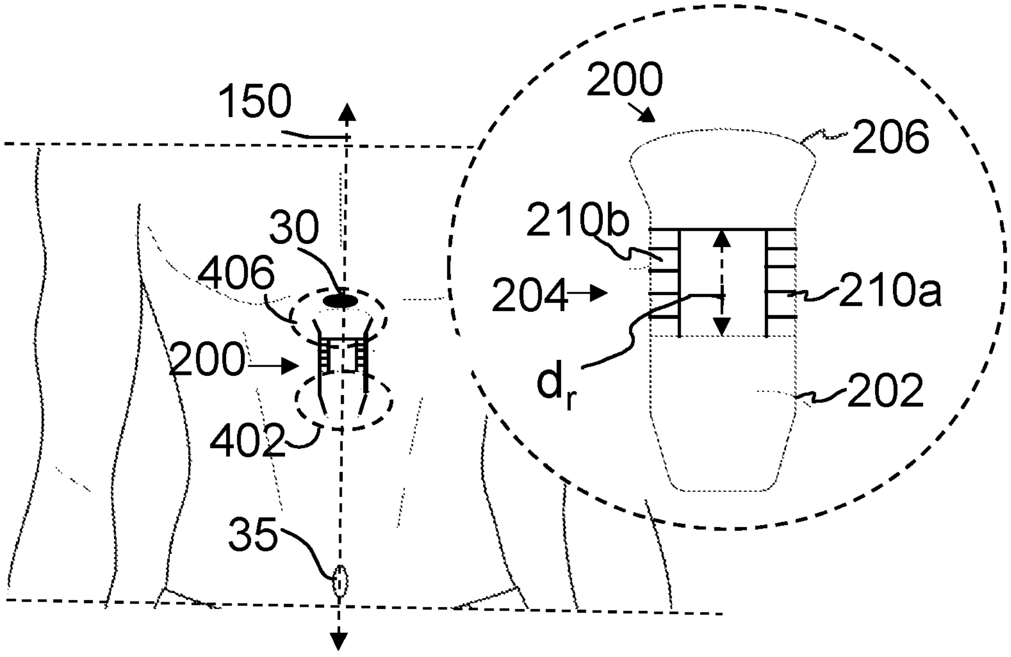
FIGS. 4A-4B are pictorial diagrams showing the skin-force sensor of FIGS. 2A-2C disposed on a user's abdominal region.
Figure 4B:
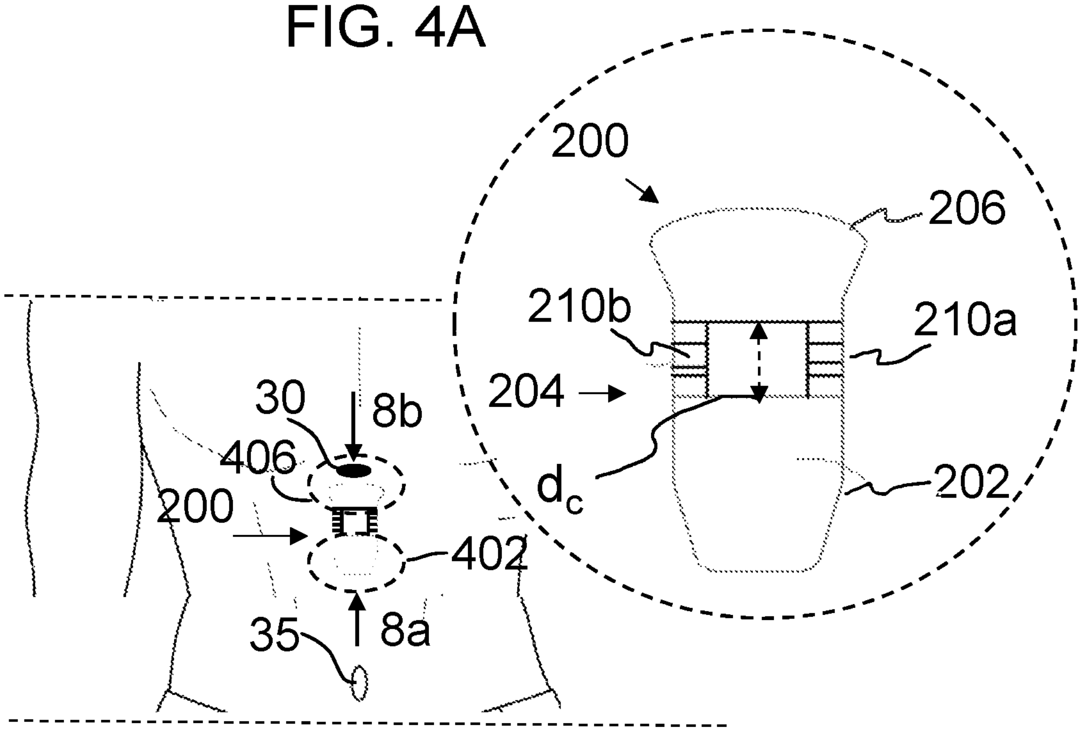

FIGS. 4A AND 4B are pictorial diagrams skin-force sensor 200 disposed on a user's abdomen to detect a deviation of the user's posture from a reference posture. As noted above, skin-force sensor 200 alone only detects the deviation of the user's posture. It does not by itself provide tactile feedback in response to detecting the deviation.

FIG. 4A shows skin-force sensor 200 applied to the user's abdomen with the user in the reference posture depicted in FIG. 1A and skin-force sensor 200 in the resting state shown in FIG. 2A. Skin-force sensor 200 is oriented with a central longitudinal axis 150 of the device generally aligned with a central longitudinal axis 250 of the user's body (as shown in FIG. 3A) between the Xiphoid process 30 and the navel 35.

Proximal sensor portion 202 is adhered to a corresponding portion of the skin on the user's abdomen, e.g., skin portion 402. Distal sensor portion 206 is likewise adhered to a corresponding portion of the user's skin, e.g., skin portion 406. In the resting state, proximal sensor portion 202 is spaced from distal sensor portion 206 by a distance dr. Distance dr corresponds to the length of elastic intermediate parts 210a, 210b in their resting states.

FIG. 4B illustrates the user in a slouching posture as illustrated in FIG. 1B. This posture deviates from the reference posture depicted in FIG. 1A. When the user slouches the natural curvature of the user's spine increases from its curvature in the upright sitting position. The abdominal muscles exert a compression force **8*a* in an upward direction on skin portion 402, and a compression force 8*b* in a downward direction on skin portion 406. Compression forces 8*a*, 8*b* on skin portions 402, 406 push proximal sensor portion 202 toward distal sensor portion 206. Elastic intermediate portion 204 contracts in response to the relative motion of proximal sensor portion 202 and distal sensor portion 206, thereby decreasing the separation distance to dc. In that manner, skin-force sensor 200** detects deviation of the user's posture from the reference posture when applied to the user's abdomen.

Figure 5:
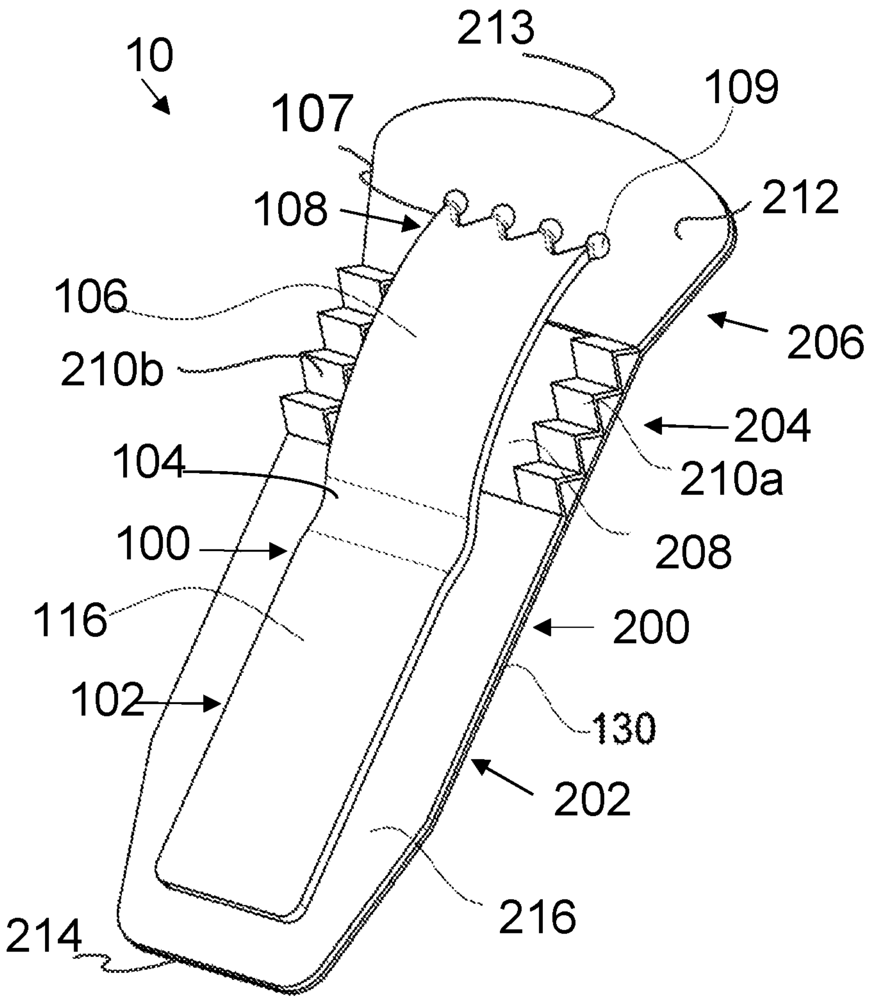
FIG. 5 is a perspective view of a posture training device including the skin-force sensor illustrated in FIGS. 2A-2C.

FIG. 5 is a perspective view of an example a posture training device 10 comprising the skin-force sensor 200 as shown in FIGS. 2-4. Posture training device 10 further comprises a tactile feedback arm 100 coupled to skin-force sensor 200. Tactile feedback arm 100 is configured to cooperate with skin-force sensor 200 to deliver tactile feedback to the user when skin-force sensor 200 detects the user's posture deviating from the reference posture as described above.

Tactile feedback arm 100 comprises a proximal arm portion 102, a bendable intermediate portion 104 and a distal arm portion 106. In some implementations, tactile feedback arm 100 comprises an elongate strip of a deformable and reformable metal material. The term 'deformable' refers to the ability of a part to undergo transformation from a reference configuration or shape to a current configuration or shape. The term 'reformable' refers to the ability of the part to undergo transformation from the current configuration back to the reference configuration, or to some other current configuration.

In some implementations proximal arm portion 102 comprises a generally flat strip having an upper planar surface 116 and a lower planar surface (not visible). The lower planar surface is rigidly affixed to an upper planar surface 216 of proximal sensor portion 202 so as to prevent relative movement therebetween. For example, the lower planar surface of proximal arm portion 102 may be bonded to the upper planar surface 216 of proximal sensor portion 202 by an adhesive such as super glue. In alternative embodiments lower planar surface of proximal arm portion 102 may be coupled to upper planar surface 216 using Velcro™.

Distal arm portion 106 includes a terminal end 108. In some implementations, terminal end 108 is formed to define respective prongs 107 projecting therefrom. In some implementations, respective prongs 107 include corresponding respective rounded tips 109 removably attached thereto.

In some implementations bendable intermediate portion 104 is manually deformable and reformable to adjust a degree of bending. In some implementations distal arm portion 106 has a generally arcuate shape (best illustrated in FIG. 7). Distal arm portion 106 is formed to span rectangular opening 208 when skin-force sensor 200 is in its resting state as shown in FIG. 5. Distal arm portion 106 may be manually deformable and reformable to adjust a degree of its arc.

Distal arm portion 106 is configured to extend from bendable intermediate portion 104 toward distal sensor portion 206 and is shaped to arc across rectangular opening 208 of elastic intermediate portion 204. Distal arm portion 106 is sufficiently long to permit placement of prongs 107 of terminal end 108 (or rounded tips 109) in slidable contact with an upper surface 212 of distal sensor portion 206 at a desired position to calibrate device 10.

Bendable intermediate portion 104 and distal arm portion 106 are deformable with respect to one another so as to bias terminal end 108 in contact with upper surface 212 when device 10 is in a reference (resting) operational state. FIG. 5 shows posture training device 10 in its ready operational state. Posture training device 10 is in its ready operational state when skin-force sensor is in its resting state (best illustrated in FIG. 2A) and terminal end 108 is in contact with upper surface 212.

In some example implementations components of device 10 illustrated herein can be formed of a thin rubber material which may be non-allergenic, e.g., a latex free rubber material. In alternative embodiments, portions of device 10 may be formed of a plastic material, which may be a clear plastic material that is sufficiently pliable and flexible to comfortably conform to the contours of the user's body.

Figure 6:
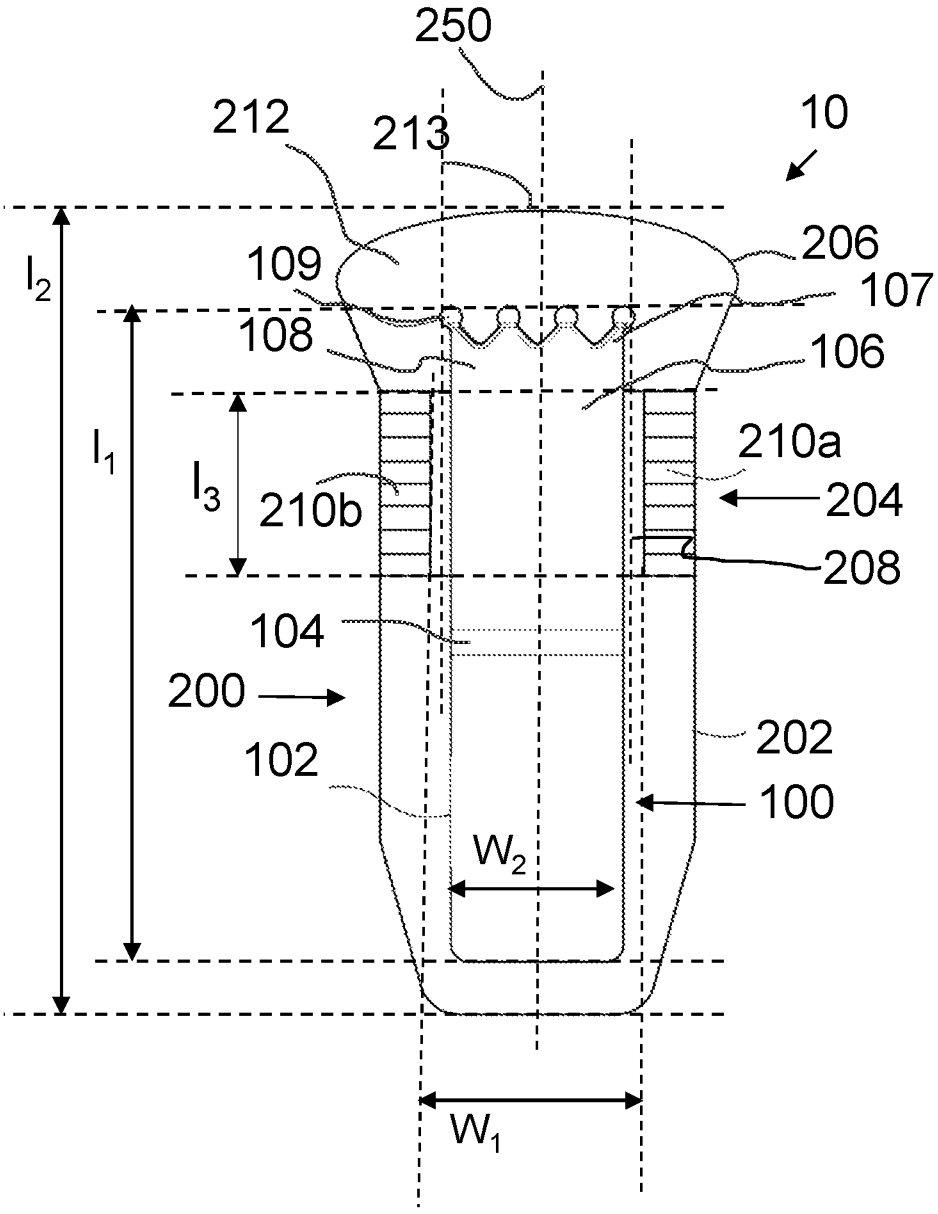
FIG. 6 is a top view of the posture training device of FIG. 5.

FIG. 6 is a top plan view showing further details of posture training device 10 shown in FIG. 5. Tactile feedback arm 100 is constructed to have a fixed length $l_1$ which is shorter than $l_2$ of skin-force sensor 200 when skin force sensor 200 is in its resting state. However, length $l_2$ of skin-force sensor 200 changes when the user deviates from the reference posture. Length $l_2$ decreases when intermediate portion 304 contracts and increases when elastic intermediate portion 204 lengthens.

Figure 8A:
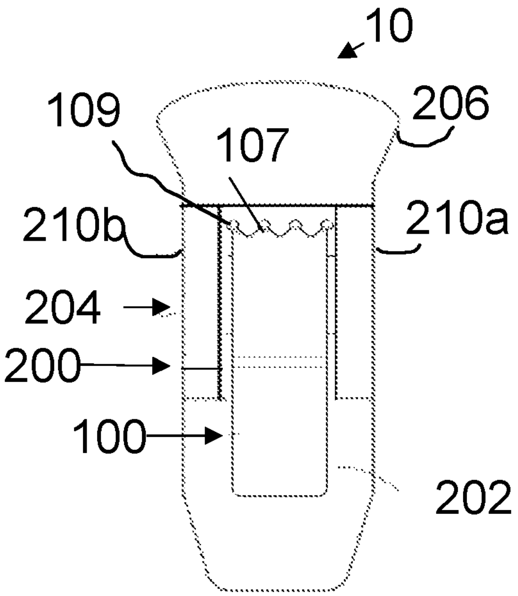
FIGS. 8A-8B are top plan views showing feedback states of the posture training device of FIG. 5.
Figure 8B:
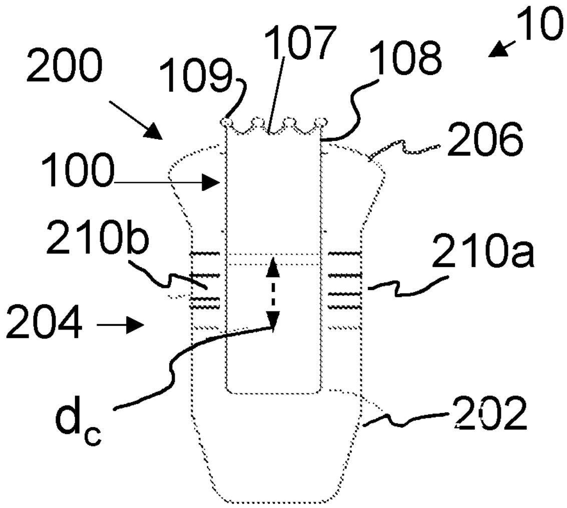

When length $l_2$ decreases due to contraction forces, terminal end 108, including prongs 107 and rounded tips 109 (if attached) slide on upper surface 212 toward, and then past edge 213 and ultimately, onto the user's skin. This feedback state is illustrated in FIG. 8B.

When length $l_2$ increases due to expansion forces, terminal end 108, including prongs 107 and rounded tips 109 (if attached) slide on surface 212 toward opening 208 in elastic intermediate portion 204, and ultimately into opening 208 thereby contacting the user's skin exposed to opening 208. This feedback state is illustrated in FIG. 8A.

Terminal end 108 of tactile feedback arm 100 has a width $W_2$ at opening 208. Opening 208 has a width $W_1$. In order to allow terminal end 108 and prongs 107 (and rounded tips 109 if attached) to fall into opening 208, width $W_1$ is greater than width $W_2$. In some examples rectangular opening 208 is a rectangular opening having an area given by $l_3 \times W_1$ in the ready operational state. However, length $l_3$ changes as length $l_2$ changes. Accordingly, the area of rectangular opening 208 decreases in response to compressing forces and increases in response to expanding forces, In some implementations, respective prongs 107 are formed to project from terminal end 108 at an angle that ensures prongs 107 (or rounded tips 109 if attached) contact the skin of user 1 to deliver tactile feedback to the user's skin when device 10 enters the activate feedback state. In some implementations respective rounded tips 109 may be attached to or disposed upon corresponding respective prongs 107 to provide comfortable tactile feedback and to permit slidable re-engagement of terminal end 108 with upper surface 212 in response the user restoring their posture to the reference posture subsequent to the user deviating from the reference posture.

Bendable intermediate portion 104 and distal arm portion 106 are each manually deformable to permit adjustment of a degree of bend of bendable intermediate portion 104 with respect to a degree of arc of distal arm portion 106. This relative adjustment permits adjustment of the position at which rounded tips 109 contact upper surface 212. This in turn determines the extent of the deviation from the reference posture that must occur before device 10 enters the active tactile feedback operational state. In other words, the position of the terminal end on upper surface 212 determines the extent to which the user's posture must deviate from the reference posture before terminal end 108 slides over edge 213 of distal sensor portion 206. This is adjustable by changing the point at which terminal end 108 contacts upper surface 212 when device 10 is in the resting operational state.

Figure 7:
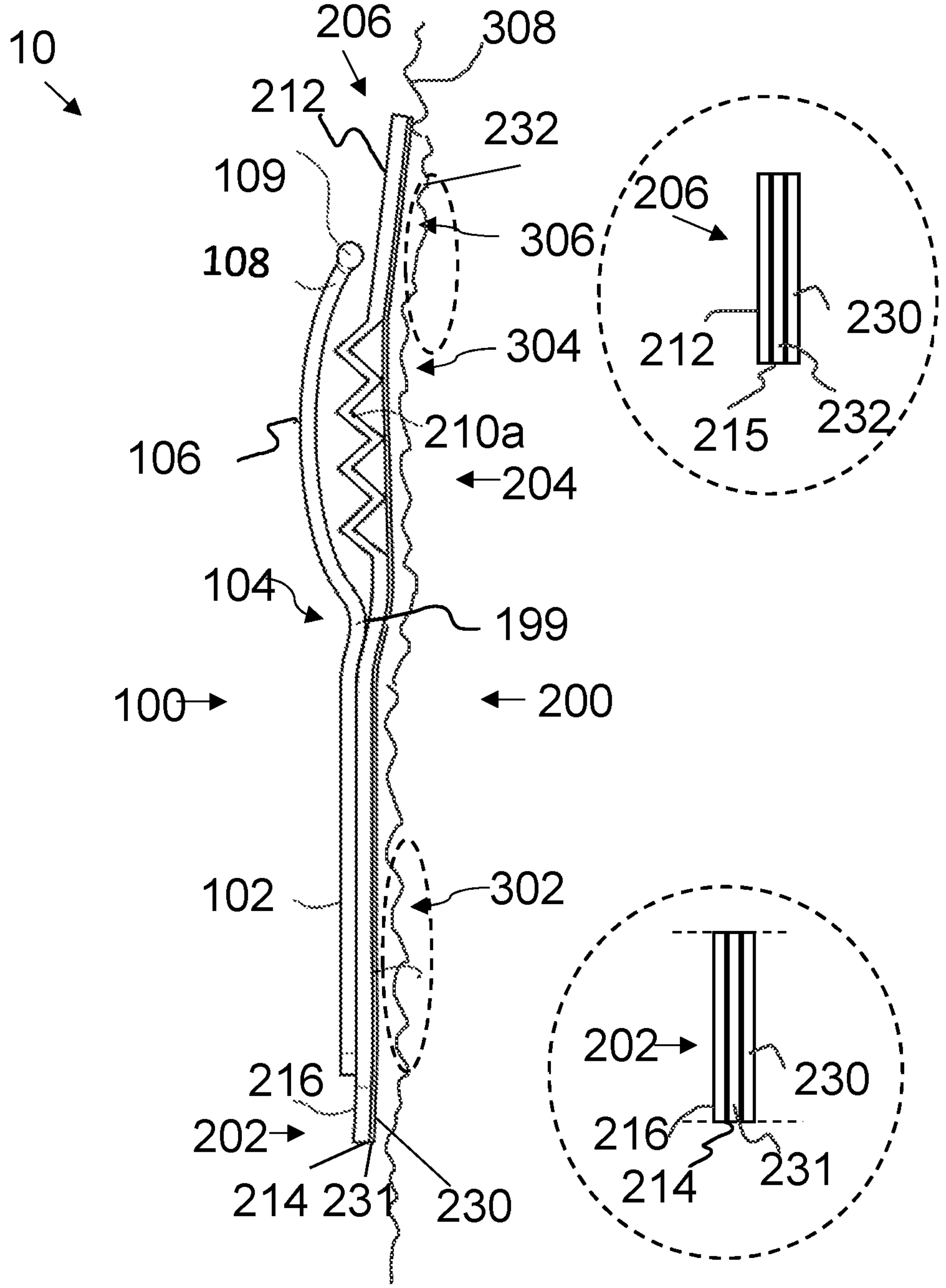
FIG. 7 is a side elevation view of the posture training device of FIG. 5.

FIG. 7 is a side elevation view of the example posture training device 10 shown in FIGS. 1-3 in a ready operational state. Proximal sensor portion 202 has an upper planar surface 216 and a bottom surface 214. Bottom surface 214 is provided with an adhesive layer 231 for adhering proximal sensor portion 202 to a corresponding skin portion 302 of user 1. Likewise, a bottom surface 215 of distal sensor portion 206 is provided with an adhesive layer 232 for adhering distal sensor portion 206 to a corresponding skin portion 306 of user 1. First and second elastic parts 210*a* and 210*b* (only 210*a* visible in FIG. 4) of elastic intermediate portion 204 are free of adhesive.

To cover adhesive layers 231 and 232 when device 10 is not in use, a removable nonallergenic waxed paper skin 230 is applied to cover adhesive layers 231, 232. Waxed paper skin 230 may extend the length of skin-force sensor 200 from proximal sensor portion 202 to distal sensor portion 206. Waxed paper skin 230 is easily removable to expose adhesive layers 231, 232 in preparation for attaching proximal sensor portion 202 and distal sensor portion 206 to the skin portions 302 and 306 respectively.

Figure 9A:
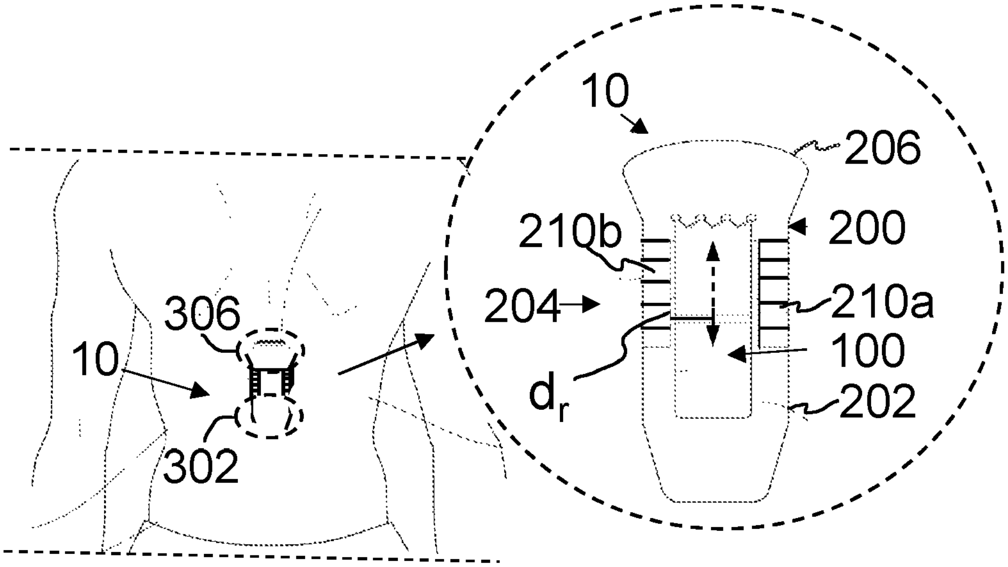
FIGS. 9A-9B are pictorial diagrams showing the posture training device of FIG. 5 disposed on a user's back.
Figure 9B:
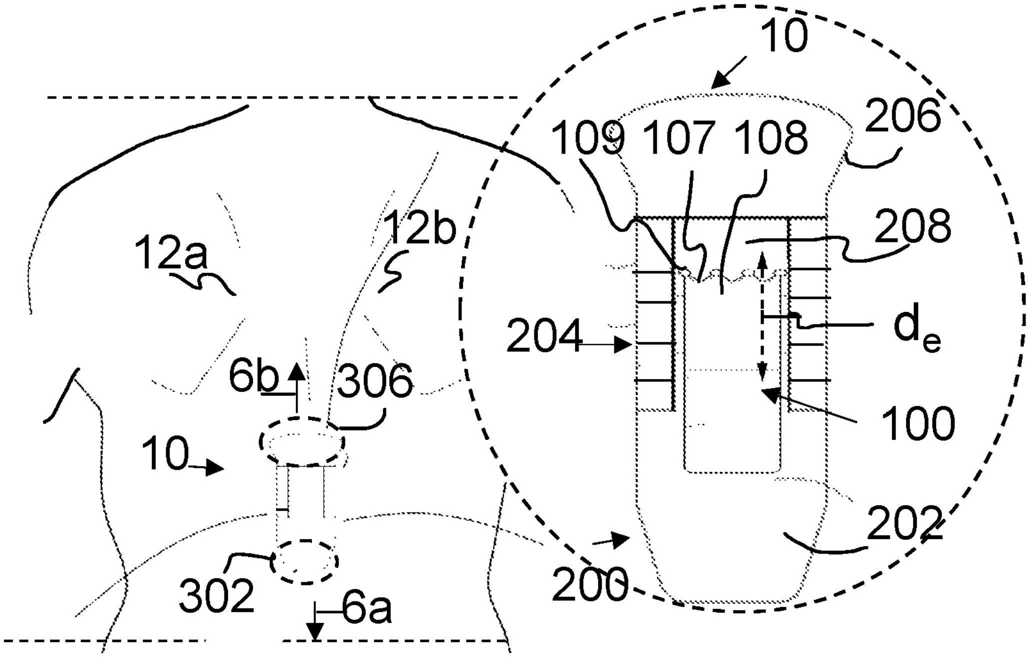

FIGS. 9A-9B are pictorial diagrams illustrating posture training device 10 applied to a user's back. FIG. 9A shows posture training device 10 applied to the user's back with the user in the reference posture depicted in FIG. 1A and device 10 in the ready operational state shown in FIG. 6. As shown in FIGS. 3A and 4A, device 10 is disposed on the users back with a central longitudinal axis 150 of the device generally aligned with a central longitudinal axis 250 of the user's body between the user's scapula 12*a*, 12*b*.

Proximal sensor portion 202 is adhered to a corresponding portion of the skin on the user's back, e.g., skin portion 302. Distal sensor portion 206 is likewise adhered to a corresponding portion of the user's skin, e.g., skin portion 306. In the resting state, proximal sensor portion 202 is spaced from distal sensor portion 206 by a distance dr (illustrated in FIG. 2A). Distance dr corresponds to the length of elastic intermediate parts 210*a*, 210*b* in their resting states.

FIG. 9B illustrates the user in a slouching posture as illustrated in FIG. 1B. This posture deviates from the reference posture depicted in FIG. 1A. When the user slouches the natural curvature of the user's spine increases from its curvature in the upright sitting position. The back muscles exert a pulling force 6*b* in an upward direction on skin portion 306, and a pulling force 6*a* in a downward on skin portion 302. Pulling forces 6*a*, 6*b* on skin portions 302, 306 pull proximal sensor portion 202 away from distal sensor portion 206. Elastic intermediate portion 204 expands in response to the relative motion of proximal sensor portion 202 and distal sensor portion 206 thereby increasing to de (expansion distance) the distance separating proximal sensor portion 202 and distal sensor portion 206.

In response to the expansion, terminal end 108, including prongs 107 and rounded tips 109 (if attached) slide on upper surface 212 toward opening 208 and ultimately enter opening 208 thereby contacting the user's skin. This feedback state is illustrated in FIG. 8A.

Figure 10A:
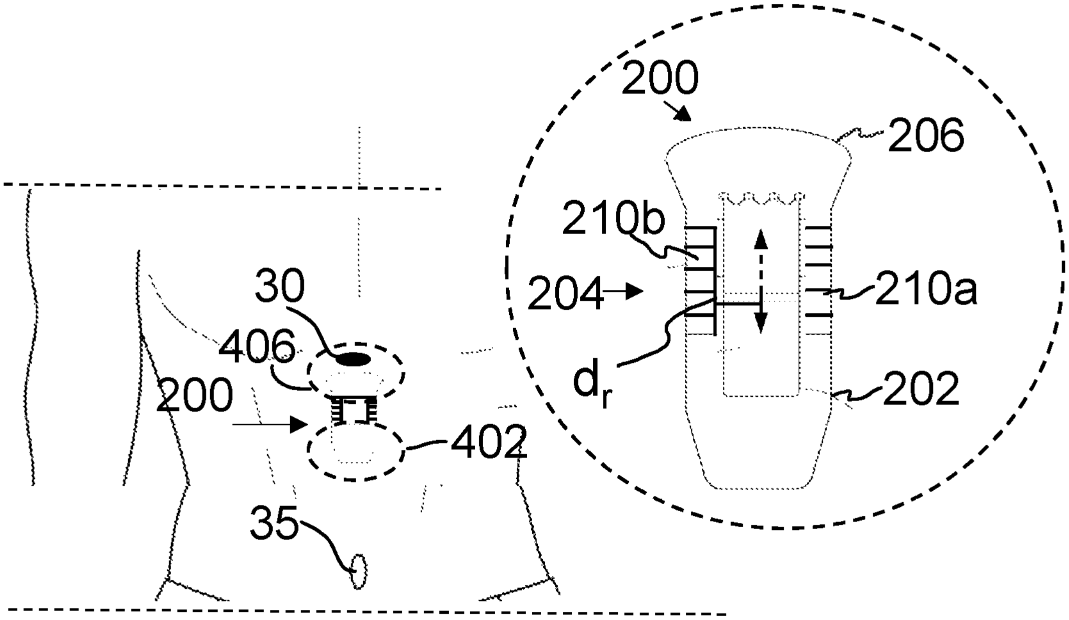
FIGS. 10A-10B are pictorial diagrams showing the posture training device of FIG. 5 disposed on a user's abdomen.
Figure 10B:
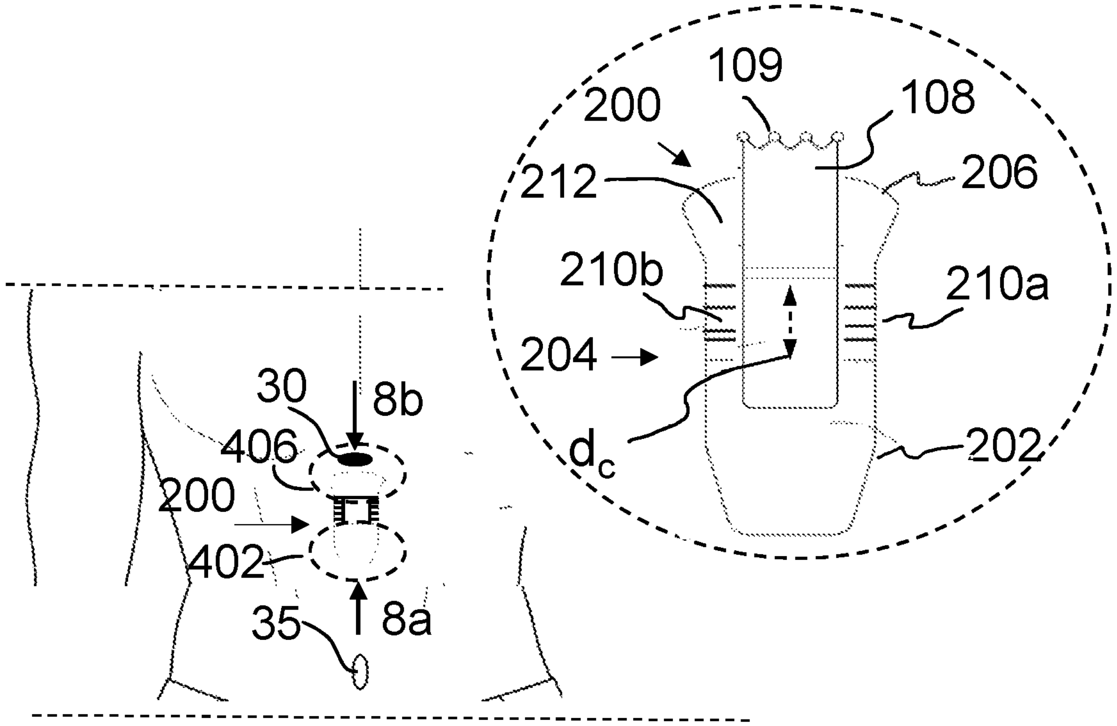

FIGS. 10A and 10B are pictorial diagrams illustrating application of posture training device 10 to a user's abdominal region. FIG. 10A shows proximal sensor portion 202 is adhered to a corresponding portion of the skin on the user's abdomen, e.g., skin portion 402. Distal sensor portion 206 is likewise adhered to a corresponding portion of the user's skin, e.g., skin portion 406. In the resting state, proximal sensor portion 202 is spaced from distal sensor portion 206 by a distance dr (illustrated in FIG. 2A). Distance dr corresponds to the length of elastic intermediate parts 210*a*, 210*b* in their resting states.

FIG. 10B shows user 1 in a posture that deviates from the user's reference posture. In the example of FIG. 10B user 1 is slouching or hunching such that the natural curvature of the user's spine has increased from its curvature in the upright sitting position, thereby decreasing the distance between the Xiphoid process 30 and navel 35 of the user with reference to the distance in the reference posture shown in FIG. 10A (also illustrated in FIG. 1B).

The skin of user 1 in the abdominal region has contracted due to slouching, thereby exerting a compressing force 8*a* on proximal sensor portion 202 via skin portion 402, and force 8*b* on distal sensor portion 206 via skin portion 406.

Device 10 maintains terminal end 108 in fixed relationship with proximal arm portion 102 and proximal sensor portion 202 via the rigid connection between them. Therefore, terminal end 108 cannot maintain its contact with upper surface 212 as distal sensor portion 206 moves toward proximal sensor portion 202 in response to compressing forces 8*a*, 8*b*. When the distance between the Xiphoid process 30 and navel 35 of user 1 decreases sufficiently to move distal sensor portion 206 behind terminal end 108, terminal end 108 will break contact with upper surface 212 and move into biased contact with the user's skin. In that manner, device 10 alerts the user to the deviation of the user's posture from the reference posture.

Should the user respond to the alert by straightening their posture, i.e., by engaging their muscles to increase the distance between Xiphoid process 30 and navel 35, elastic intermediate portion 204 will unfold as proximal sensor portion 202 and distal sensor portion 206 move away from one another. Distal sensor portion 206 will slidably engage terminal end 108 urging terminal end 108 into biased contact with upper surface 212, thereby removing the tactile contact with the user's skin and restoring device 10 to its ready operational state (shown in FIG. 6). The removal of the tactile contact serves to inform the user that they have successfully restored their reference posture. In that manner, device 10 trains the user to maintain the reference posture.

Figure 11:
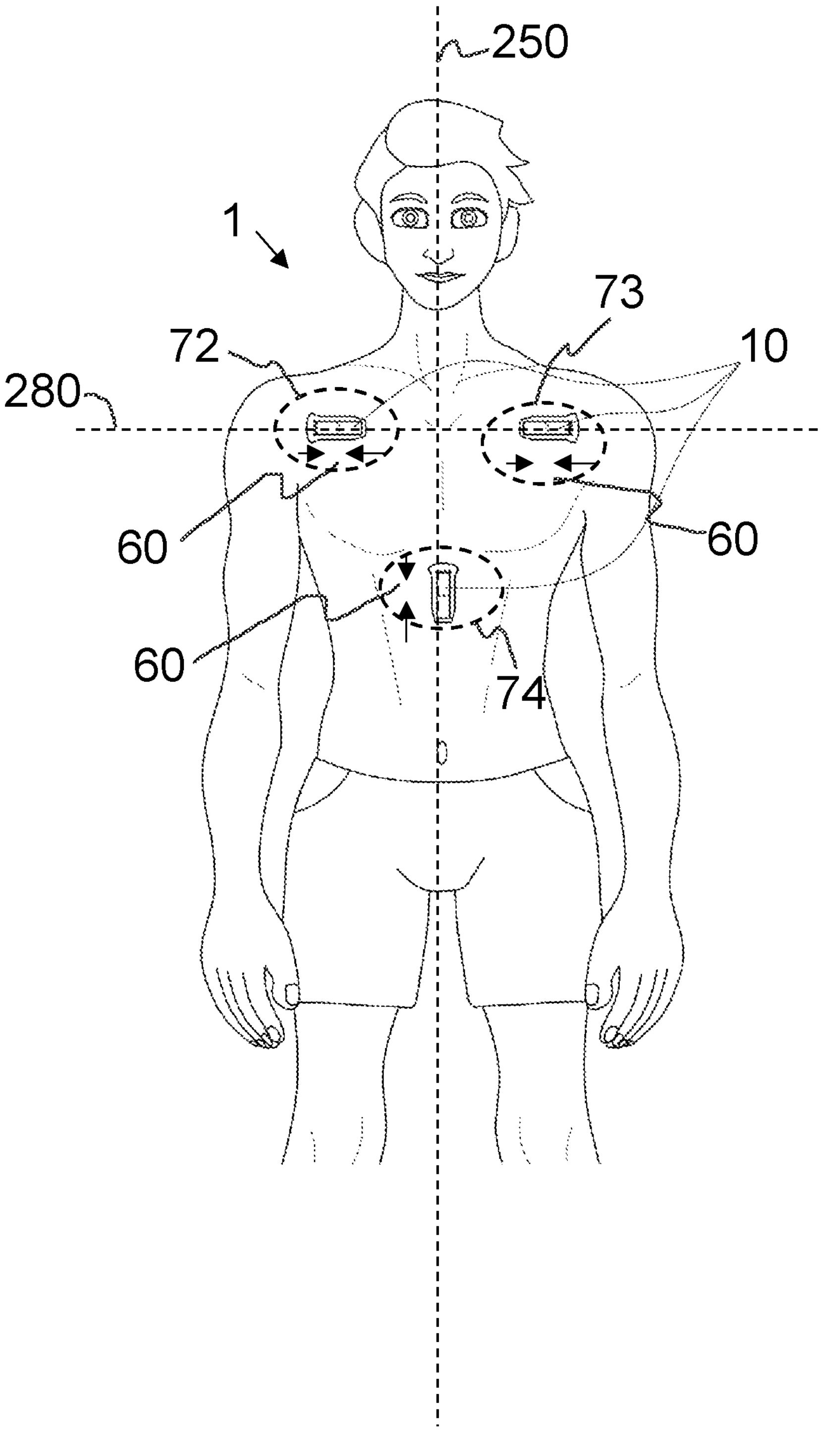
FIG. 11 is a pictorial diagram showing a plurality of posture training devices disposed on a user.

FIG. 11 is a pictorial diagram illustrating a plurality of devices 10 disposed about a user's body. Devices 10 are shown in their ready operational state which corresponds to an upright reference posture, which may be an upright sitting reference posture as illustrated in FIG. 1B. in the example of FIG. 11 a first device 10 is applied to an area 72 proximal a right front shoulder joint of user 1 such that the longitudinal axis of first device 10 extends along a lateral axis 280 of the body of user 1. In this orientation, first device 10 is situated to experience a compressing force 60 exerted on device 10 by contraction of the skin in area 72 when user 1 deviates from the reference posture, e.g., by rounding the right shoulder forward. In that case, first device 10 will respond as described above to deliver a tactile feedback to the skin of user 1 in area 72.

A second device 10 is applied to an area 73 proximal a left shoulder joint of user 1 such that the longitudinal axis of second device 10 extends along a lateral axis of the body of user 1. In this orientation, second device 10 is situated to experience a compressing force 60 when user 1 deviates from the reference posture, e.g., by rounding the left shoulder forward. In that case, second device 10 will respond as described above to deliver a tactile feedback to the skin of user 1 in area 73.

A third device 10 is applied to an abdominal area 74 as shown in FIG. 6 such that the longitudinal axis of third device 10 extends along the central longitudinal axis 250 of the body of user 1. The operation of each of devices 10 is described above with respect to FIGS. 10A and 10B.

Figure 12:
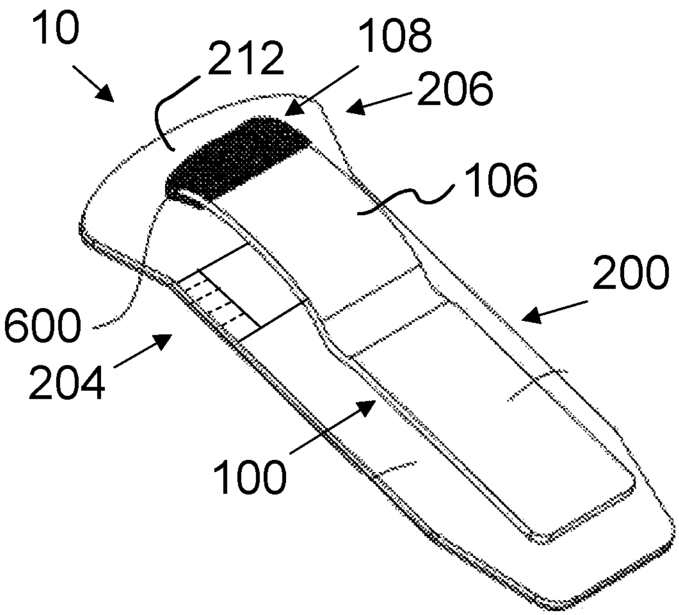
FIG. 12 is a perspective view of the posture training device of FIG. 5 including an alternative implementation of a tactile arm.

FIG. 12 is a perspective view of an example posture training device 10 as shown in FIG. 5. In the example of FIG. 12 terminal end 108 of distal arm portion 106 is covered with a soft cloth piece 600. The cloth piece 600 may be disposed on terminal end 108 and arranged to substantially surround respective rounded tips 109 (not visible in FIG. 12).

In some implementations posture training device 10 includes a brush clamp 900 as illustrated in FIGS. 13A-13C. FIG. 13A shows brush clamp 900 comprises a rectangular top clamp member 950 and a rectangular bottom clamp member 920. Rectangular top clamp member 950 includes bristles 913 adhered to a front side 911. Rectangular bottom clamp member 920 includes bristles 914 adhered to a bottom side 954. Brush clamp 900 is configured to engage terminal end 108 of tactile feedback arm 100 between top clamp member 950 and bottom clamp member 920.

FIG. 13B is a side elevation view of brush clamp 900 including bristles 913 adhered to front side 911 and bristles 914 adhered to bottom side 954. As shown in FIG. 4 distal arm portion 106 is formed to bias bristles 914 against upper surface 212 of distal sensor portion 206.

FIG. 13C shows further details of rectangular top clamp member 950 and rectangular lower clamp member 920 including hinge 955. Rectangular top clamp portion 950 is formed to define respective openings 902 for engaging at least top portions of corresponding respective rounded tips 109 at terminal end 108 of distal arm portion 106. Rectangular lower clamp member 920 is formed to define respective openings 901 to receive respective lower portions of rounded tips 109.

Top clamp member 950 includes a locking pin 903. Bottom claim member 920 includes a locking pin receptacle 904. In use, terminal end 108 of tactile feedback arm 100 is manipulated to insert respective rounded tips 109 in corresponding respective openings 901. Top claim member 95 is lowered onto bottom clamp member 920 via hinge 955 so that respective openings 902 engage rounded tips 109 and locking pin 903 engages locking pin receptacle 904.

While the exemplary embodiments of the present invention are described and illustrated herein, it will be appreciated that they are merely illustrative. It will be understood by those skilled in the art that various modifications in form and detail may be made therein without departing from or offending the spirit and scope of the invention as defined by the appended claims. Additionally, the invention illustratively disclosed herein suitably may be practiced in the absence of any element which is not specifically disclosed herein—and in particular, embodiment specifically contemplated, is intended to be practiced in the absence of any element which is not specifically disclosed herein.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the composition or method.

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub combination or as suitable in any other described embodiment of the disclosure. Certain features described in the context of various embodiments are not to be considered essential features of those embodiments unless the embodiment is inoperative without those elements.

Although the disclosure has been described in conjunction with specific embodiments thereof, it is evident that many alternatives, modifications and variations will be apparent to those skilled in the art. Accordingly, the disclosure is intended to encompass all such alternatives, modifications and variations within its spirit and broad scope.

What is claimed is:

1. A posture training device comprising:

a skin-force sensor for detecting a deviation of a user from a reference posture, wherein the skin-force sensor comprising:

a proximal sensor portion;

a distal sensor portion; and an elastic intermediate sensor portion having a resting state corresponding to a separation distance between the proximal sensor portion and the distal sensor portion, the elastic intermediate sensor portion deforming to change the separation distance in response to the deviation of the user from the reference posture;

a tactile feedback arm, wherein the tactile feedback arm comprising:

a proximal arm portion anchored to the proximal sensor portion; a distal arm portion; and a deformable intermediate arm portion;

wherein the deformable intermediate arm portion defining a bend between the proximal arm portion and the distal arm portion;

wherein the distal arm portion includes a terminal end defined by respective prongs extending therefrom; and wherein the respective prongs include corresponding respective rounded tips configured for attachment to, and detachment from the corresponding respective prongs; and a brush, wherein the brush including:

a spine including a first side surface and a second side surface defining respective tip-engaging openings configured to removably engage the corresponding respective rounded tips to permit attachment and detachment of the brush from the terminal end; and a first bristle-bearing piece affixed to a third side surface of the spine such that bristles of the first bristle-bearing piece extend in a direction of the respective prongs when the corresponding respective rounded tips are engaged in the respective tip-engaging openings.

2. The device of claim 1 further comprising a cloth portion disposed on the terminal end and arranged to substantially surround the corresponding respective rounded tips.

3. A posture training device comprising:

a skin-force sensor for detecting a deviation of a user from a reference posture, wherein the skin-force sensor comprising:

a proximal sensor portion;

a distal sensor portion; and an elastic intermediate sensor portion having a resting state corresponding to a separation distance between the proximal sensor portion and the distal sensor portion, the elastic intermediate sensor portion deforming to change the separation distance in response to the deviation of the user from the reference posture;

a tactile feedback arm, wherein the tactile feedback arm comprising:

a proximal arm portion anchored to the proximal sensor portion; a distal arm portion; and a deformable intermediate arm portion;

wherein the deformable intermediate arm portion defining a bend between the proximal arm portion and the distal arm portion;

wherein the distal arm portion includes a terminal end defined by respective prongs extending therefrom;

furthermore, the deformable intermediate arm portion and the distal arm portion are configured to bias the terminal end against an upper surface of the distal sensor portion when the elastic intermediate sensor portion is at rest; and wherein the elastic intermediate sensor portion further comprises:

a first elastic part extending between the proximal sensor portion and the distal sensor portion along a first side of the skin-force sensor; and a second elastic part extending between the proximal sensor portion and the distal sensor portion along a second side of the skin-force sensor opposite the first side; and the first elastic part and the second elastic part being laterally spaced apart to define an opening in the elastic intermediate sensor portion through which a portion of a user's skin is exposed to the tactile feedback arm.

4. The device of claim 3 wherein the deformable intermediate arm portion and the distal arm portion are configured to bias the terminal end of the distal arm portion into contact with an exposed skin portion in response to a relative movement in a first direction between the proximal sensor portion and the distal sensor portion.

5. The device of claim 4 wherein the deformable intermediate arm portion and the distal arm portion are configured to bias the terminal end into a contact with an uncovered skin portion in response to the relative movement between the proximal sensor portion and the distal sensor portion in a second direction opposite the first direction.

6. The device of claim 5 wherein the skin-force sensor further comprises:

a first adhesive layer provided to a lower surface of the proximal sensor portion for anchoring the proximal sensor portion to a first skin portion; and a second adhesive layer provided to a lower surface of the distal sensor portion for anchoring the distal sensor portion to a second skin portion of the user's skin.

7. The device of claim 6 wherein the exposed skin portion is intermediate the first skin portion and the second skin portion, and the second skin portion is intermediate the exposed skin portion and the uncovered skin portion when the proximal sensor portion is anchored to the first skin portion and the distal sensor portion is anchored to the second skin portion.

8. The device of claim 7 wherein:

the elastic intermediate sensor portion is at rest in a reference posture of the user;

the user's skin is in a reference state when the user is in the reference posture; and the user's skin expands from the reference state in response to musculoskeletal expansion forces applied to the user's skin when a posture of the user deviates from the reference posture such that the first and second skin portions move in a direction away from each other, whereby the terminal end of the tactile feedback arm loses the contact with the upper surface of the distal sensor portion and is biased into contact with an exposed skin portion via an opening in the elastic intermediate sensor portion.

9. The device of claim 8 wherein the user's skin exerts a compression force on the proximal sensor portion and the distal sensor portion when a posture of the user deviates from the reference posture such that the first and second skin portions move in a direction toward from each other, whereby the terminal end of the tactile feedback arm loses the contact with an upper surface of the distal sensor portion and is biased into contact with the uncovered skin portion.

* * * * *